United States Patent
Bertz et al.

(10) Patent No.: US 9,503,416 B2
(45) Date of Patent: Nov. 22, 2016

(54) COMMUNICATION SYSTEM TO PROVIDE SELECTIVE ACCESS TO A WIRELESS COMMUNICATION DEVICE

(71) Applicant: Sprint Communications Company L.P., Overland Park, KS (US)

(72) Inventors: Lyle T. Bertz, Lee's Summit, MO (US); Charles Brent Hirschman, Overland Park, KS (US); Christian Erik Seagren, Pleasanton, KS (US)

(73) Assignee: Sprint Communications Company L.P., Overland Park, KS (US)

( * ) Notice: Subject to any disclaimer, the term of this patent is extended or adjusted under 35 U.S.C. 154(b) by 48 days.

(21) Appl. No.: 14/678,451

(22) Filed: Apr. 3, 2015

(65) Prior Publication Data

US 2015/0215273 A1    Jul. 30, 2015

Related U.S. Application Data

(63) Continuation of application No. 13/910,636, filed on Jun. 5, 2013, now Pat. No. 9,030,965.

(51) Int. Cl.
| | |
|---|---|
| *H04W 4/00* | (2009.01) |
| *H04L 29/12* | (2006.01) |
| *H04W 74/00* | (2009.01) |
| *G01K 13/00* | (2006.01) |
| *G01N 33/00* | (2006.01) |
| *G01R 21/00* | (2006.01) |
| *G01W 1/00* | (2006.01) |
| *H04L 29/08* | (2006.01) |
| *H04W 4/02* | (2009.01) |
| *H04L 29/06* | (2006.01) |

(52) U.S. Cl.
CPC .............. *H04L 61/20* (2013.01); *G01K 13/00* (2013.01); *G01N 33/004* (2013.01); *G01R 21/00* (2013.01); *G01W 1/00* (2013.01); *H04L 61/1511* (2013.01); *H04W 74/006* (2013.01); *H04L 67/325* (2013.01); *H04L 69/28* (2013.01); *H04W 4/025* (2013.01)

(58) Field of Classification Search
CPC combination set(s) only.
See application file for complete search history.

(56) References Cited

U.S. PATENT DOCUMENTS

| | | |
|---|---|---|
| 5,805,820 A | 9/1998 | Bellovin et al. |
| 2003/0014524 A1 | 1/2003 | Tormasov |
| 2007/0300077 A1 | 12/2007 | Mani et al. |

(Continued)

OTHER PUBLICATIONS

Colitti et al, REST Enabled Wireless Sensor Networks for Seamless Integration with Web Applications, IEEE, 2011.*

(Continued)

*Primary Examiner* — Frank Duong

(57) ABSTRACT

A communication system provides selective access to target wireless communication devices. A naming server system receives naming system registration messages from target wireless communication devices and address requests from user devices. The naming server system determines if the current time is within the access schedule for the target wireless communication device. If the current time is within the access schedule for the target wireless communication device, then the naming server system returns the address for the target wireless communication device. If the current time is not within the access schedule for the target wireless communication device, then the naming server system will respond with a timeframe when the target wireless communication device will be available for access.

20 Claims, 6 Drawing Sheets

(56) References Cited

U.S. PATENT DOCUMENTS

2010/0306351 A1* 12/2010 Lee .................... H04L 29/1232
709/220
2014/0162684 A1* 6/2014 Shaw ...................... H04W 4/02
455/456.1

OTHER PUBLICATIONS

Jeroen Hoebeke, et al.; "Leveraging upon standards to build the Internet of Things;" Communications and Vehicular Technology in the Benelux, 2012 IEEE 19th Symposium; Nov. 16, 2012; pp. 1-6; Department of Information Technology, Ghent University; Ghent, Belgium.

Isam Ishaq, et al.; "Facilitating sensor deployment, discovery and resource access using embedded web services;" Innovative Mobile and Internet Services in Ubiquitous Computing, 2012 Sixth International Conference; Jul. 4, 2012; pp. 717-724; Department of Information Technology, Ghent University; Ghent, Belgium.

J. Nieminen, et al.; "Configuration and service discovery of IPv6 capable sensors;" draft-nieminen-core-service-discovery-00; Oct. 24, 2011; pp. 1-11; Internet-Draft; Universitat Politecnica de Catalunya, Barcelona, Spain.

* cited by examiner

COMMUNICATION SYSTEM TO PROVIDE SELECTIVE ACCESS TO A WIRELESS COMMUNICATION DEVICE

RELATED CASES

This patent application is a continuation of U.S. patent application Ser. No. 13/910,636 filed on Jun. 5, 2013 and titled "A COMMUNICATION SYSTEM TO PROVIDE SELECTIVE ACCESS TO A WIRELESS COMMUNICATION DEVICE." U.S. patent application Ser. No. 13/910,636 is hereby incorporated by reference into this patent application.

TECHNICAL BACKGROUND

Domain names are data strings that can be used to access resources over data networks. The domain names are often selected to ease user retention of the name. A prime example of a domain name is "uspto.gov" for the U.S. Patent Office. A Domain Naming System (DNS) stores and serves information associated with domain names. A prime example of the associated information is the current Internet Protocol (IP) addresses that can be used to communicate with resources in the domain. A common task for a DNS is the translation of domain names into their corresponding IP addresses. For example, a DNS would translate uspto.gov into the IP address of a Patent Office server system. The user then communicates with the Patent Office over the Internet using the IP address.

To load the DNS, Internet servers register their IP addresses with the DNS in association with their domain names. While these registrations are active, the DNS will serve out the IP addresses in response to queries having the domain names. Eventually, a given IP address registration may time-out, and the DNS will require another registration before serving out the IP address. In other scenarios, a properly registered IP address may still fail the user due to another reason, such as network or server problems. In addition to the IP address, the DNS may associate other information with the domain names, such as call state and network state.

Wireless communication devices are increasingly being used as content servers that interact with the DNS to provide their content over the Internet (or a private IP network). For example, a wireless camera having a domain name and an IP address may register the name and IP address with the DNS to serve out live images from the camera. These wireless communication devices may have limited availability due to power restraints, network availability, and the like. Unfortunately, the wireless devices and the DNS are not properly configured for efficient and effective interaction in the developing wireless environment.

TECHNICAL OVERVIEW

A communication system provides selective access to target wireless communication devices. A naming server system receives naming system registration messages from target wireless communication devices and address requests from user devices. The naming server system determines if the current time is within the access schedule for the target wireless communication device. If the current time is within the access schedule for the target wireless communication device, then the naming server system returns the address for the target wireless communication device. If the current time is not within the access schedule for the target wireless communication device, then the naming server system will respond with a timeframe when the target wireless communication device will be available for access.

DETAILED DESCRIPTION

Figure 1:
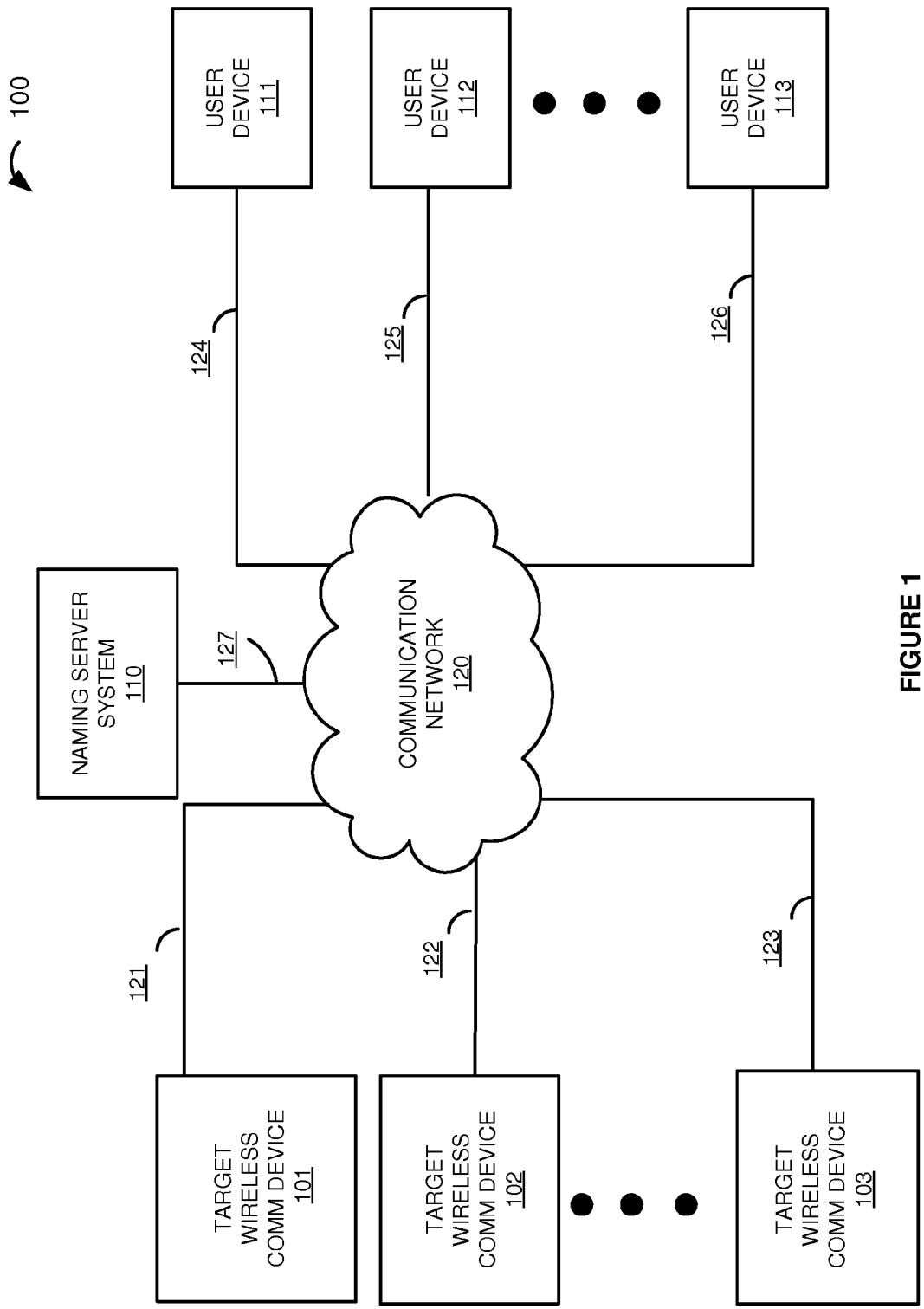
FIG. 1 illustrates a communication system to provide selective access to a wireless communication device.

FIG. 1 illustrates communication system 100 that provides selective access to target wireless communication devices 101-103. Communication system 100 comprises: target wireless communication devices 101-103 (also referred to herein as "target devices"), naming server system 110, user devices 111-113, communication network 120, and communication links 121-127. Target wireless communication devices 101-103 might be phones, computers, cameras, sensors, or some other machine having wireless transceivers and control circuitry.

In communication system 100, target wireless communication devices 101-103 register their names and network addresses with naming server system 110. The registrations also include access schedules. Naming server system 110 serves out the network addresses and/or future access timeframes to user devices 111-113 based on the access schedule.

Figure 2:
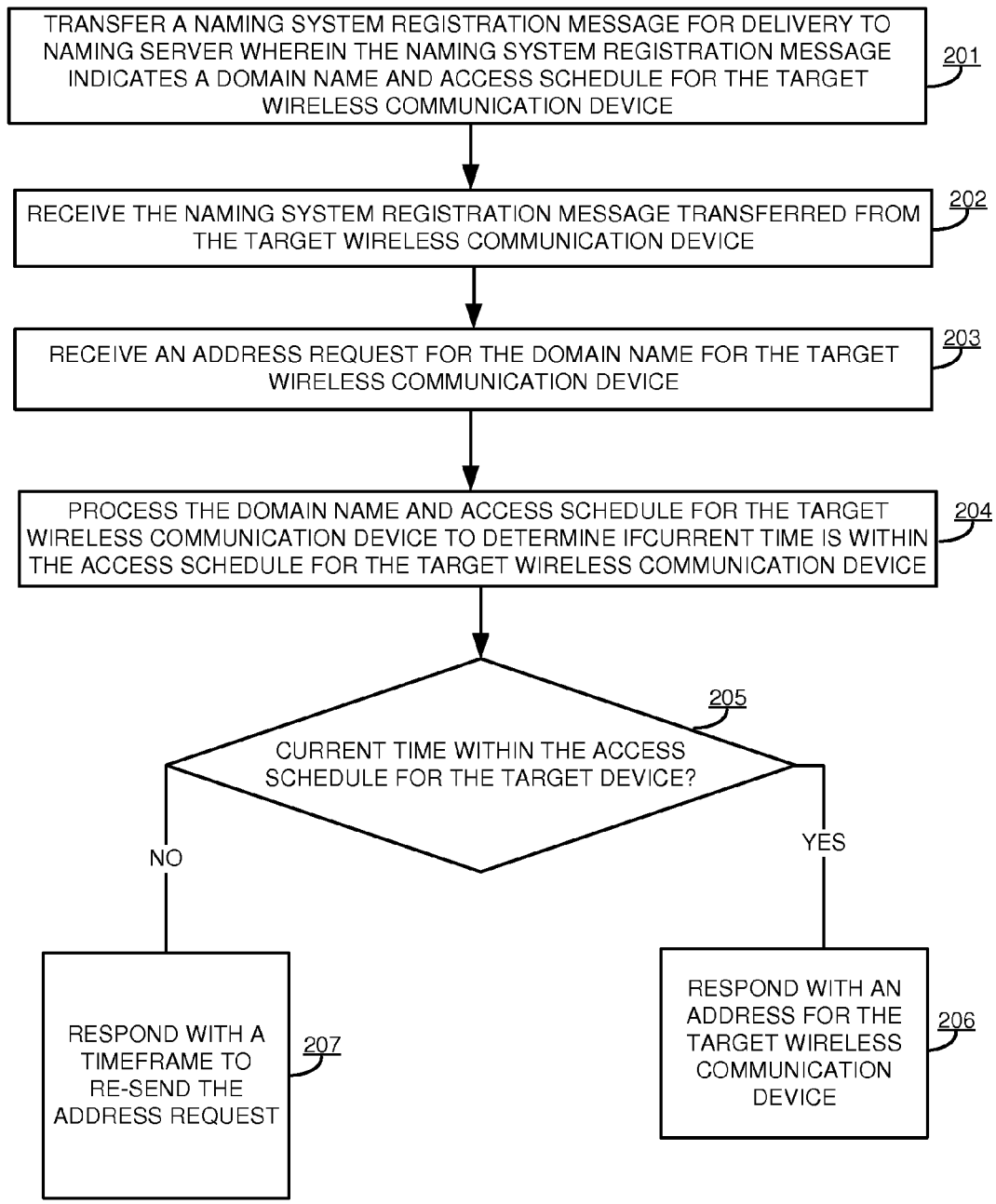
FIG. 2 illustrates the operation of a communication system to provide selective access to a wireless communication device.

FIG. 2 illustrates the operation of communication system 100 to provide selective access to target wireless communication devices 101-103. Target wireless communication devices 101-103 transfer naming system registration messages (also referred to herein as "registration messages") for delivery to naming server system 110 (201). The naming system registration messages indicate the associated domain names and access schedules for target devices 101-103. The naming system registration messages may also indicate network addresses for target devices 101-103, although the network addresses could be provided later.

Note that a single target device may have multiple names, addresses, and access schedules, or that multiple target devices may share names, addresses, and access schedules. The domain names comprise data strings, such as Uniform Resource Identifiers (URIs) and the like. The access schedules control whether naming server system 110 serves out the network addresses, or whether naming system 110 suggests a subsequent timeframe to obtain the network address from naming system 110. Typically, the access schedules correspond to when target devices 101-103 will have adequate content, power, and network connectivity.

Naming server system 110 receives the naming system registration messages transferred by target wireless communication devices 101-103 (202). Naming server system 110 stores the provided data in association with the respective domain name. One example of naming server system 110 is a DNS server, although other naming server systems could be used.

Naming server system 110 receives address requests from user devices 111-113 (203). The address requests indicate the domain names for target wireless communication devices 101-103. Naming server system 110 processes the domain names and their associated access schedules to determine whether the current time is within the access schedules for the target wireless communication devices (204). If naming server 110 determines that the current time is within the access schedule of the target wireless communication device (205), then naming server system 110 responds with the address for the target wireless communication device (206). If naming server system 110 determines that the current time is not within the access schedule of the target wireless communication device (205), then naming server system 110 responds with a timeframe to re-send the address request (207).

In the above operation, target wireless communication devices 101-103 and naming server system 110 effectively and efficiently interact to conserve resources across communication system 100. Target wireless communication devices 101-103 are not required to maintain the overly burdensome content, power, or network connectivity that is required to remain on-net. User devices 111-113 are not required to continually request address translations until the target devices become available. Likewise, naming server system 110 should also handle a lower amount of failed address requests. In addition, communication network 120 handles a lower amount of failed address requests to naming server system 110. Communication network 120 also handles a lower amount of failed data transmissions that are directed to unavailable the target devices.

In some examples, the access schedule is a simple predetermined set of time periods, such as 9:00-11:00 PM on Mondays and Fridays. In other examples, the access schedule reflects an estimated future time when the target device expects to have adequate power, presence at a location, network connectivity, content access, and the like. In yet other examples, the access schedule reflects a calculated time-to-live for the target device power supply, presence at a location, estimated event time, network connectivity, and the like. In further examples, the access schedule is determined based on a trigger for the target device, such as: atmospheric conditions, temperature, wind speeds, motion, presence in a geographic location, network status, radio frequency network, and the like.

Consider an example where the target wireless device is solar powered sensor with limited battery capacity. Due to the amount of sun and usage, the battery power varies. The target device may then vary its access schedule in accord with changing solar and usage conditions. For example, the target device may reduce the length of time content is served during periods of reduced sun or periods of increased power usage.

Some target devices may trigger data availability based on conditions. For example, a target atmospheric sensor may register for 2-hours of content access starting in twelve hours in response to extreme $CO_2$ levels. A target security camera may register for ten minutes of content access starting immediately in response to unauthorized motion detection.

Figure 3:
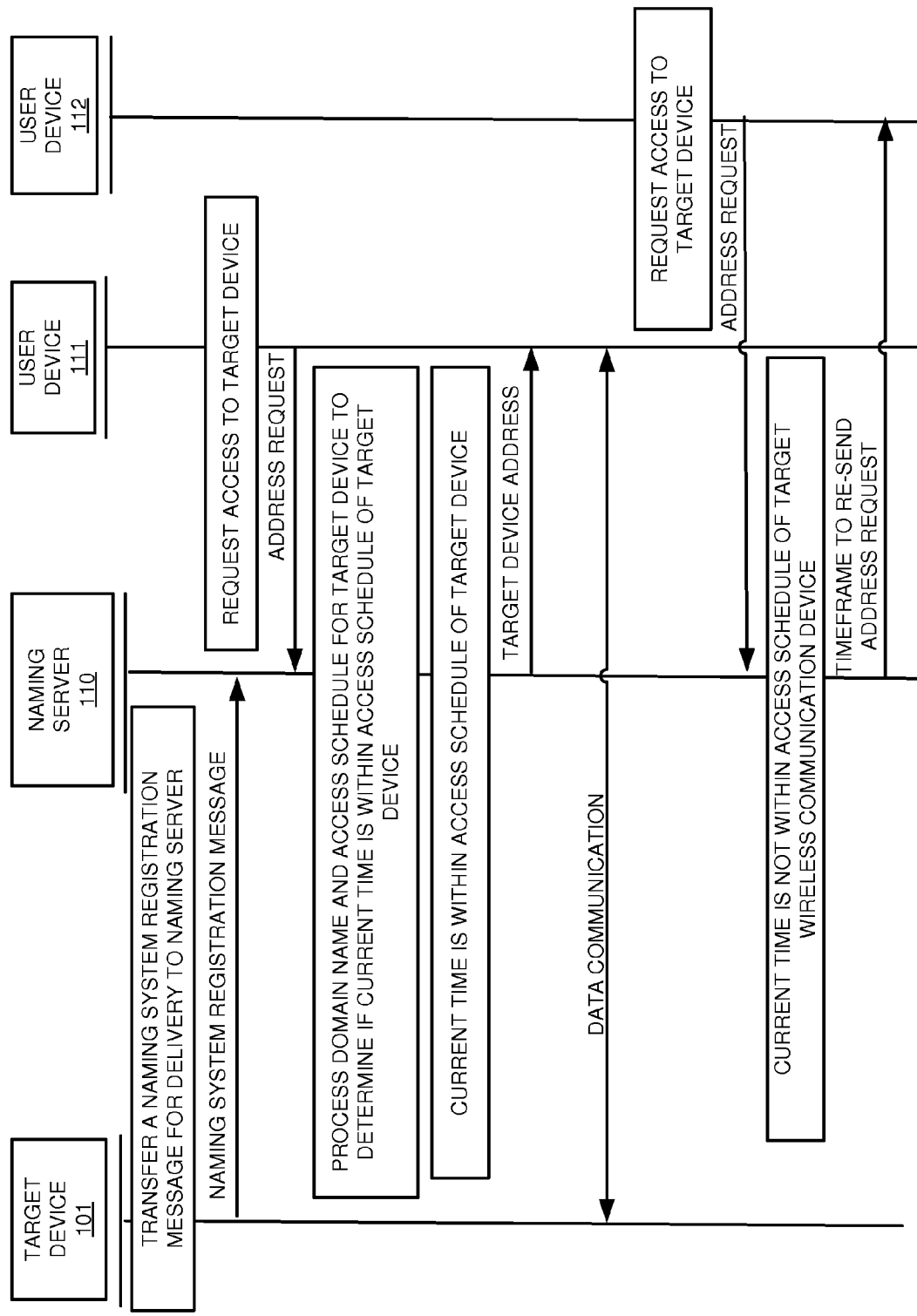
FIG. 3 illustrates an operation of the communication system to provide selective access to a wireless communication device.

FIG. 3 illustrates an operation of communication system 100 to provide selective access to target wireless communication devices 101-103. Naming server system 110 receives a naming system registration message from target wireless device 101. The naming system registration message indicates a domain name and includes an access schedule for target wireless device 101. Naming server system 110 also receives an address request from user device 111. Naming server system 110 compares the current time with the access schedule for target wireless device 101. Since the current time is within the access schedule for target wireless device 101, naming server system 110 sends the network address for target wireless device 101 to user device 111. Later user device 112 requests access to target wireless device 101. Naming server system 110 compares the current time with the access schedule for target wireless device 101. The current time is no longer within the access schedule for target wireless device 101, so naming server system 110 responds with a timeframe when user device 112 should retry the address query.

Figure 4:
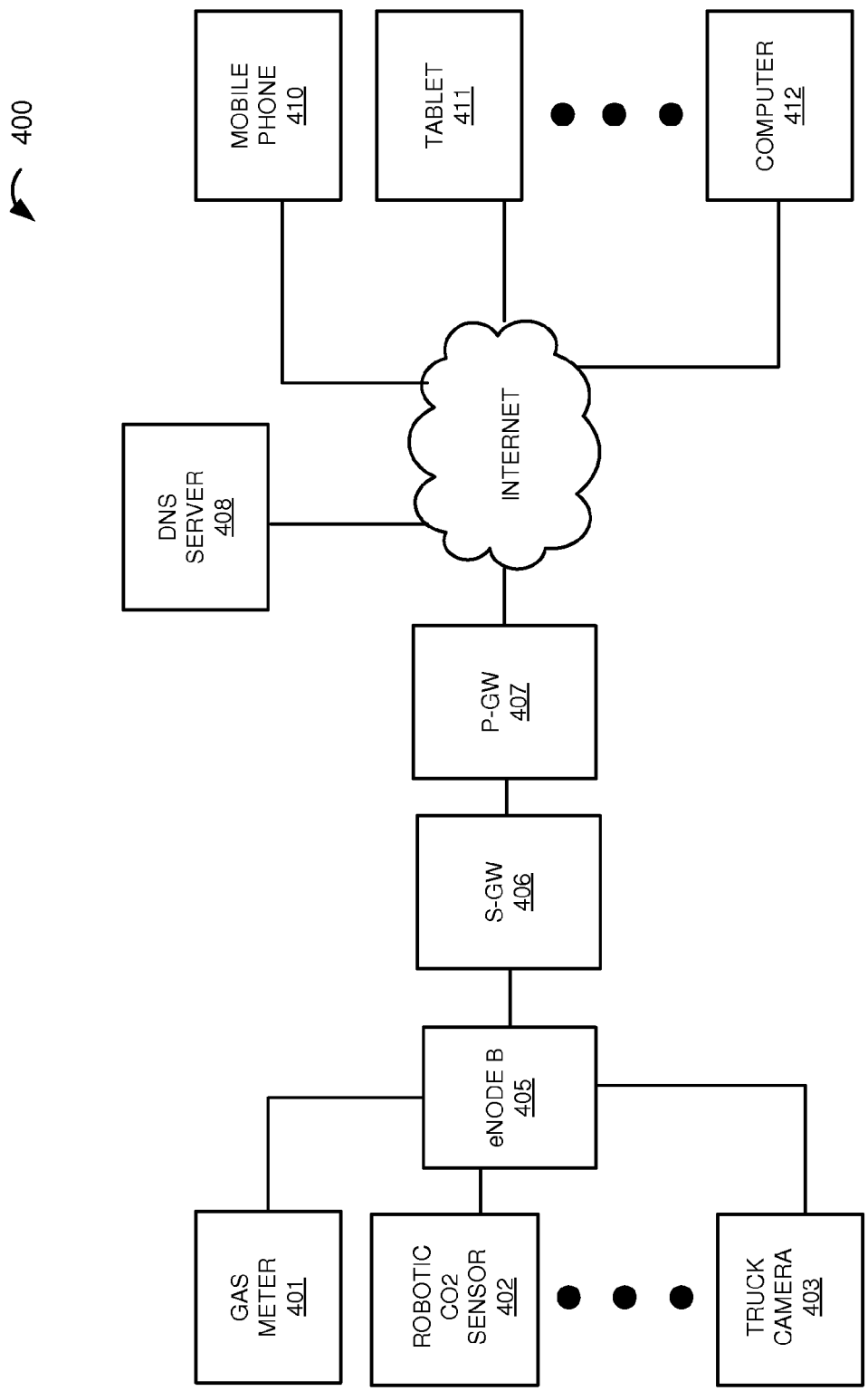
FIG. 4 illustrates an LTE communication system to provide selective access to a wireless communication device.

FIG. 4 illustrates Long Term Evolution (LTE) communication system 400 to provide selective access to wireless devices 401-403. LTE communication system 400 provides an example of communication system 100, although communication system 100 may use alternative configurations and operations. LTE communication system 400 comprises target devices 401-403, eNodeB 405, S-GW 406, P-GW 407, DNS server 408, and user devices 410-412. Target devices 401-403 comprise a gas meter, robotic $CO_2$ sensor, and truck camera. User devices 410-412 comprise a mobile phone, tablet, and computer.

In some examples, gas meter 401 is programmed to be available on the 26th day of each month for ten minutes between 11:49 PM and 11:59 PM. Gas meter 401 registers with DNS server 408 with an access schedule that indicates these available time periods. If DNS server 408 receives an address request for gas meter 401 before 11:49 on the 26th of the month, then DNS server 408 responds with the timeframe when a DNS retry should be attempted—between 11:49 PM and 11:59 PM on the 26th day of the month. When the current time reaches 11:49 PM on the 26th day of the month, then DNS server 408 will begin to serve out the IP address of gas meter 401. Thus, computer 412 may obtain the IP address of access gas meter 401 to download information for billing purposes. If DNS server 408 receives an address request for gas meter 401 after 11:59 on the 26th of the month, then DNS server 408 responds with the timeframe when a DNS retry should be attempted—between 11:49 PM and 11:59 PM on the 26th day of the next month. If desired, the domain name and IP address would be available for use by other gas meters before and after 11:49 PM and 11:59 PM on the 26th day of the month. In this way content downloads can be batched and staggered for multiple gas meters.

In another example, robotic $CO_2$ sensor 402 determines its access schedule based on an estimated future time for arrival in a geographic area. This could be calculated based on distance and speed of travel. Robotic $CO_2$ sensor 402 would register with DNS server 408 to start serving its IP address after its estimated time of arrival. As a result, DNS server 408 will provide the estimated time of arrival in response to address queries for robotic $CO_2$ sensor 402 until the current time reaches the estimated time.

Alternatively, robotic $CO_2$ sensor 402 may wait until it reaches the geographic area to register. Once robotic $CO_2$ sensor 402 detects that is within the geographic area, sensor 402 would then register with DNS server 408 to begin serving its IP address immediately and for another 2 hours—the length of time that robotic $CO_2$ sensor 402 remains within the geographic area. DNS translations during this 2-hour time period would indicate the IP address for robotic $CO_2$ sensor 402 and indicate the time-to-live at that geographic location.

In some examples, DNS server 408 will notify tablet 411 that robotic $CO_2$ sensor 402 is available. In other examples, robotic $CO_2$ sensor 402 may arrive at a specified geographic location but need to recharge its battery and will not be available until after a specified time to recharge. Different factors, such as type of power supply, remaining power, network connectivity, content, geographic location, and the like, may be considered in determining the access schedule for robotic $CO_2$ sensor 402. Alternatively, rather than determining the access schedule based on detecting the device's presence in a pre-determine geographic location, robotic $CO_2$ sensor 402 may determine the access schedule based an estimated future time when robotic $CO_2$ sensor 402 will be within range of a pre-determined radio frequency (i.e. a carrier's base station) or when network load is expected to be low.

In another example, robotic $CO_2$ sensor 402 registers when it detects $CO_2$ levels above a threshold. The access schedule for robotic $CO_2$ sensor 402 is based on when registration is triggered and exact timeframes may not be known in advance. In addition, the response provided by DNS server 408 may also indicate the time remaining to access robotic $CO_2$ sensor 402 (i.e. "device will be available for ten more minutes"). This could be based on power usage and remaining battery power among other factors. In yet another example, robotic $CO_2$ sensor 402 powers on and records content when $CO_2$ levels are above a threshold. Robotic $CO_2$ sensor 402 then registers when the device memory storage is at 80% capacity or when battery power is at 15% remaining.

In another example, truck camera 403 determines its access schedule based on scheduled departure/arrival time and travel time. At the scheduled departure time, truck camera 403 powers on and registers with DNS server 408. The access schedule for truck camera 404 may indicate that truck camera 403 will be available for the duration of the trip (i.e. "4 hours"). In other examples, truck camera 403 registers with DNS server 408 when it detects it is located within a pre-determined geographic area and remains registered while located within a specified geographic area. Alternatively, truck camera 403 powers up and registers with DNS server 408 when it detects it is in motion and does not de-register until it has been stationary for a specified amount of time.

In some examples, truck camera 403 is accessible only by authorized users. The access schedule for truck camera 403 indicates a list of approved users in addition to the timeframe(s) that truck camera 403 is available. In this example, the list of approved users includes tablet 411 and computer 412, but not mobile phone 410. When mobile phone 410 requests access to truck camera 403, DNS server 408 determines mobile phone 410 is not on the list of approved users. DNS server 408 responds that access is denied. When computer 412 requests access during a time that is within the access schedule for truck camera 403, DNS server 408 responds with the IP address for truck camera 403.

Figure 5:
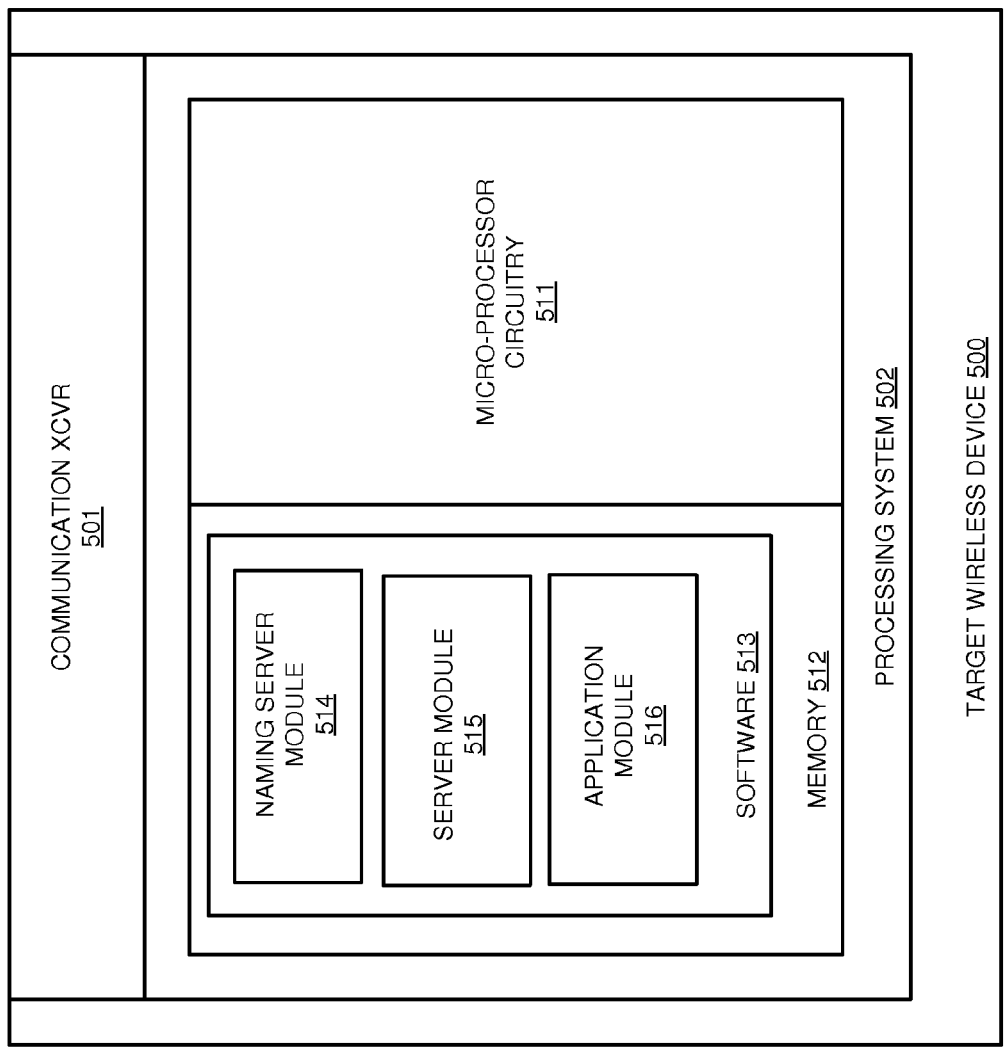
FIG. 5 illustrates a wireless communication device that interacts with a naming system to allow selective access.

FIG. 5 illustrates a target wireless communication device 500 that interacts with a naming system to allow selective access. Target wireless device 500 is an example of the target wireless devices 101-103 and 401-403, although these devices may use alternative configurations and operations. Target wireless device 500 comprises communication transceiver 501 and processing system 502. Processing system 502 includes processing circuitry 511 and memory 512 that stores software 513. Software 513 comprises software modules 514-516.

Communication transceiver 501 comprises communication components, such as antennas, amplifiers, filters, modulators, signal processing circuitry, software, and the like. Communication transceiver 501 may be configured to use IP, Ethernet, and various wireless protocols—including combinations thereof. Communication transceiver 501 transfers registration messages to a naming server system and transfers requested content to requesting devices.

Processing circuitry 511 comprises microprocessor and other circuitry that retrieves and executes operating software 513 from memory system 512. Processing circuitry 511 may comprise a single device or could be distributed across multiple devices—including devices in different geographic areas. Processing circuitry 511 may be embedded in various types of equipment. Examples of processing circuitry 511 include central processing units, application specific processors, and logic devices, and/or any type of computer processing devices—including combinations thereof.

Memory system 512 comprises a non-transitory computer readable storage medium readable by processing system 502 and capable of storing software 513, such as a disk drive, flash drive, data storage circuitry, or some other hardware memory apparatus—including combinations thereof. Memory system 512 can include volatile and non-volatile, removable and non-removable media implemented in any method or technology for storage of information, such as computer readable instructions, data structures, program modules, or other data—including combinations thereof. Memory system 512 may comprise a single device or could be distributed across multiple devices—including devices in different geographic areas. Memory system 512 may be embedded in various types of equipment.

Software 513 comprises computer programs, firmware, or some other form of machine-readable processing instructions. Software 513 may include an operating system, utilities, drivers, network interfaces, applications, or some other type of software. In this example, software 513 comprises: Naming Server module 514, Server module 515, and Application module 516, although software 513 could have alternative configurations in other examples.

Software 513 can be implemented in program instructions and can be executed by processing system 502. Software 513 can include additional processes, programs, or components, such as operating system software, database software, or application software—including combinations thereof. Software 513 can also comprise firmware or some other form of machine-readable processing instructions executable by processing system 502.

When executed by processing system 502, software 513 directs processing system 502 to operate as described herein to interact with naming server systems. In particular, Naming Server module 514 directs processing system 502 to transfer naming system registration messages with access schedules for delivery to a naming server system. Server module 515 directs processing system 502 to handle content requests to serve out the requested content. Application module 516 directs processing system 502 to develop content and access schedules.

Figure 6:
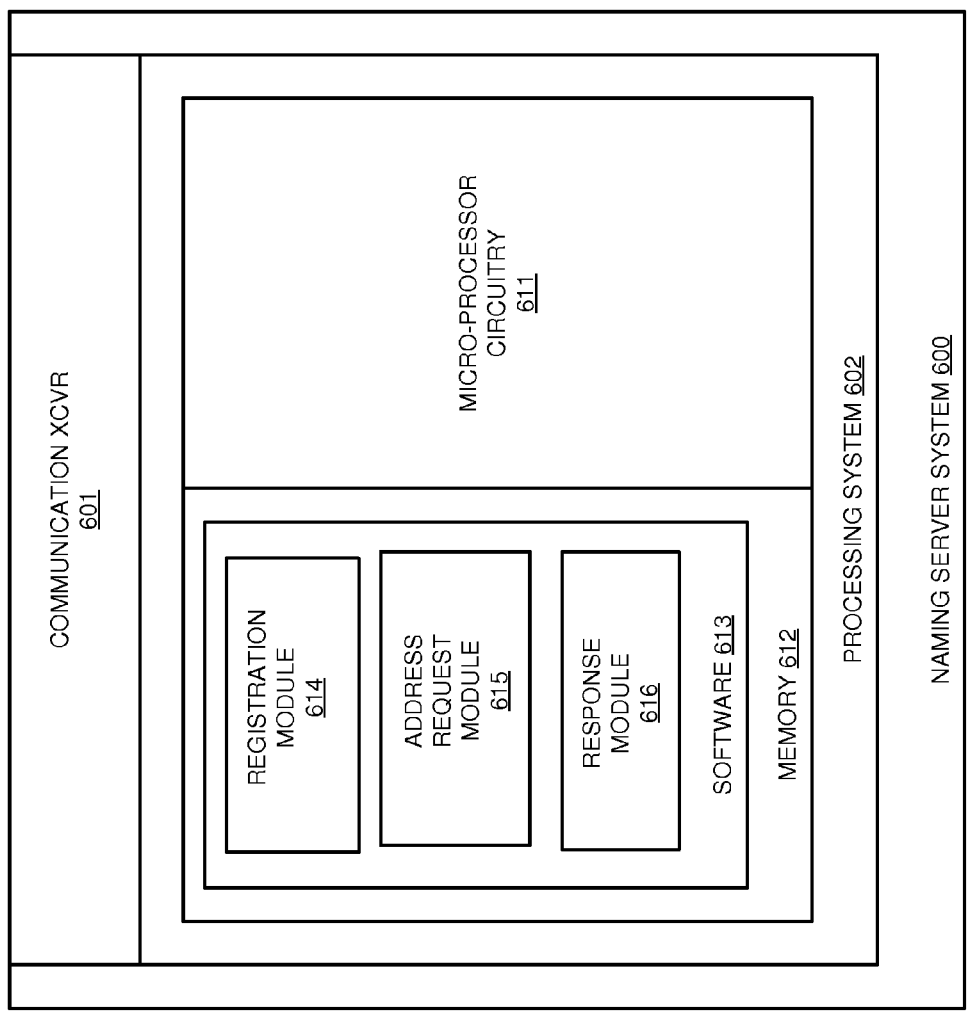
FIG. 6 illustrates a naming server system that provides selective access to wireless communication devices.

FIG. 6 illustrates naming server system 600 that provides selective access to wireless communication devices. naming server system 600 is an example of naming server system 110 and DNS server 408, although these systems may use alternative configurations and operations. Naming server system 600 comprises communication transceiver 601 and processing system 602. Processing system 602 includes processing circuitry 611 and memory 612 that stores software 613. Software 613 comprises software modules 614-616.

Communication transceiver 601 comprises components that communication over communication links such as network cards, ports, RF transceivers, processing circuitry and software, or some other communication components. Communication transceiver 601 may be configured to communication over metallic, wireless, or optical links. Communication transceiver 601 may be configured to use Time-Division Multiplexing (TDM), IP, Ethernet, optical networking, wireless protocols, communication signaling, or some other communication format—including combinations thereof. Communication transceiver 601 receives registration messages from target wireless communication devices and receives address requests from user devices.

Processing circuitry 611 comprises microprocessor and other circuitry that retrieves and executes operating software 613 from memory system 612. Processing circuitry 611 may comprise a single device or could be distributed across multiple devices—including devices in different geographic areas. Processing circuitry 611 may be embedded in various types of equipment. Examples of processing circuitry 611 include central processing units, application specific processors, and logic devices, and/or any type of computer processing devices—including combinations thereof. Processing circuitry 611 processes the domain name and access schedule for the requested target wireless communication device to determine whether the current time is within the access schedule for the target wireless communication device.

Memory system 612 comprises a non-transitory computer readable storage medium readable by processing system 602 and capable of storing software 613, such as a disk drive, flash drive, data storage circuitry, or some other hardware memory apparatus—including combinations thereof. Memory system 612 can include volatile and non-volatile, removable and non-removable media implemented in any method or technology for storage of information, such as computer readable instructions, data structures, program modules, or other data—including combinations thereof. Memory system 612 may comprise a single device or could be distributed across multiple devices—including devices in different geographic areas. Memory system 612 may be embedded in various types of equipment. In some examples, a computer apparatus could comprise memory system 612 and software 613.

Software 613 comprises computer programs, firmware, or some other form of machine-readable processing instructions. Software 613 may include an operating system, utilities, drivers, network interfaces, applications, or some other type of software. In this example, software 613 comprises Registration module 614, Address Request module 615, and Response module 616, although software 613 could have alternative configurations in other examples.

Software 613 can be implemented in program instructions and can be executed by processing system 602. Software 613 can include additional processes, programs, or components, such as operating system software, database software, or application software—including combinations thereof. Software 613 can also comprise firmware or some other form of machine-readable processing instructions executable by processing system 602.

When executed by processing system 602, software 613 directs processing system 602 to operate as described herein to provide selective access to target wireless communication devices. In particular, Registration module 614 directs processing system 602 to process the naming system registration message from target wireless communication devices to register the target wireless communication devices. Address Request module 615 directs processing system 602 to process the address requests from user devices. Response module 616 directs processing system 602 to transfer responses to the address requests.

Referring back to FIG. 1, target devices 101-103 comprise any device having wireless communication connectivity. Target devices 101-103 comprise radio frequency (RF) communication circuitry, antenna, and software elements. The RF circuitry typically includes amplifiers, filters, modulators, and signal processing circuitry. In some examples, target wireless device 101-103 includes circuitry and equipment to exchange wireless communications over wireless links with wireless access system, transfer registration requests for DNS registration, transfer access schedules, and receive access requests from user devices, among other operations. Target wireless devices 101-103 may also include user interface systems, memory devices, computer-readable storage medium, software, processing circuitry, or other communication components. Target wireless devices 101-103 may be a sensor, computer, meter, camera, vehicle, appliance, electronic device that uploads data or downloads available updates, or some other wireless communication apparatus—including combinations thereof.

Naming server system 110 comprises a processing system and communication transceiver. Naming server system 110 may also include other components such as a router, data storage system, and power supply. Naming server system 110 may reside in a single device or may be distributed across multiple devices. Naming server system 110 may be a discrete system or may be integrated within other systems—including other systems within communication system 100. In some examples, naming server system 110 could comprise a network server system, network-attached storage, storage area network, home location register, visitor location register, User devices 111-113 comprise any device having communication connectivity with hardware and circuitry programmed to function as a communication device. User devices 111-113 are used to access the target wireless communication devices. User devices 111-113 may also include user interface systems, memory devices, computer-readable storage medium, software, processing circuitry, or other communication components. User devices 111-113 may be a computer, laptop, tablet, personal digital assistant (PDA), mobile phone, cellular phone, smartphone, machine transceivers, televisions, mobile Internet devices, and/or some other apparatus having networking components—including combinations thereof.

Communication network 120 is representative and may be a single wireless network or may comprise multiple sub-networks—including wireless networks and the Internet. Communication network 120 typically includes wireless base stations, routers, servers, gateways, signaling processors, communication links, and the like.

Wireless communication links 121-123 use air or space as the transport medium. Wireless communication links 121-123 may use various protocols, such as Code Division Multiple Access (CDMA), Global System for Mobile communications (GSM), High-Speed Packet Access (HSPA), Evolution-Data Optimized (EVDO), Long Term Evolution (LTE), Worldwide Interoperability for Microwave Access (WiMax), IEEE 802.11 protocols (WIFI), Bluetooth (near-field), or some other wireless communication format— including combinations thereof. Communication links 124-127 use metal, air, space, glass, plastic, and/or some other transport material. Communication links 124-126 could use various communication protocols, such as TDM, IP, Ethernet, optical networking, hybrid fiber coax (HFC), communication signaling, wireless protocols, or some other communication format—including combinations thereof. Communication links 121-127 are representative and may include intermediate links, systems, and networks.

The above description and associated figures teach the best mode of the invention. The following claims specify the scope of the invention. Note that some aspects of the best mode may not fall within the scope of the invention as specified by the claims. Those skilled in the art will appreciate that the features described above can be combined in various ways to form multiple variations of the invention. As a result, the invention is not limited to the specific embodiment described above, but only by the following claims and their equivalents.

What is claimed is:

1. A method of operating a target wireless communication device having a device sensor to provide communication access through a naming system, the method comprising:
   detecting sensor data through the device sensor, processing the sensor data to detect a trigger condition, and determining an access schedule for the target wireless communication device;
   transferring a registration request for delivery to the naming system indicating the access schedule and a domain name for the target wireless communication device, wherein the naming system transfers a network address for the target wireless communication device responsive to address requests received within the access schedule and transfers a network address retry timeframe responsive to other address requests received outside the access schedule; and
   receiving data requests having the network address within the access schedule and responsively transferring content data for the data requests within the access schedule.

2. The method of claim 1 wherein detecting the sensor data through the device sensor comprises detecting atmospheric condition data in an atmospheric condition sensor.

3. The method of claim 1 wherein transferring the content data comprises transferring the atmospheric condition data.

4. The method of claim 1 wherein detecting the sensor data through the device sensor comprises detecting device power supply status in a power supply sensor.

5. The method of claim 1 wherein detecting the sensor data through the device sensor comprises detecting device geographic location in a geographic location sensor.

6. The method of claim 1 wherein detecting the sensor data through the device sensor comprises detecting device network connectivity in a network connectivity sensor.

7. The method of claim 1 wherein the target wireless communication device comprises a meter.

8. The method of claim 1 wherein the target wireless communication device comprises a carbon dioxide sensor.

9. The method of claim 1 wherein the target wireless communication device comprises a temperature sensor.

10. The method of claim 1 wherein the target wireless communication device comprises a camera.

11. A target wireless communication device to provide communication access through a naming system, the method comprising:
    a processing system;
    a communication transceiver to exchange data communications for the processing system;
    a device sensor to detect sensor data for the processing system;
    the processing system configured to process the sensor data to detect a trigger condition, determine an access schedule for the target wireless communication device, transfer a registration request for delivery to the naming system indicating the access schedule and a domain name for the target wireless communication device, receive data requests having the network address within the access schedule, and transfer content data for the data requests within the access schedule; and
    wherein the naming system transfers a network address for the target wireless communication device responsive to address requests received within the access schedule and transfers a network address retry timeframe responsive to other address requests received outside the access schedule.

12. The target wireless communication device of claim 11 wherein the sensor comprises an atmospheric condition sensor.

13. The target wireless communication device of claim 11 wherein the content data comprises atmospheric condition data.

14. The target wireless communication device of claim 11 wherein the device sensor comprises a power supply sensor.

15. The target wireless communication device of claim 11 wherein the device sensor comprises a geographic location sensor.

16. The target wireless communication device of claim 11 wherein the device sensor comprises a network connectivity sensor.

17. The target wireless communication device of claim 11 wherein the target wireless communication device comprises a meter.

18. The target wireless communication device of claim 11 wherein the target wireless communication device comprises a carbon dioxide sensor.

19. The target wireless communication device of claim 11 wherein the target wireless communication device comprises a temperature sensor.

20. The target wireless communication device of claim 11 wherein the target wireless communication device comprises a camera.

* * * * *